United States Patent [19]

Andrews et al.

[11] Patent Number: 4,634,698

[45] Date of Patent: * Jan. 6, 1987

[54] ANTIGLAUCOMA AGENTS

[75] Inventors: David R. Andrews, Bloomfield; Federico C. A. Gaeta, Rockaway Township, Morris County, both of N.J.

[73] Assignee: Schering Corporation, Kenilworth, N.J.

[*] Notice: The portion of the term of this patent subsequent to Dec. 3, 2002 has been disclaimed.

[21] Appl. No.: 721,015

[22] Filed: Apr. 8, 1985

Related U.S. Application Data

[63] Continuation-in-part of Ser. No. 653,186, Sep. 24, 1984, Pat. No. 4,556,655.

[51] Int. Cl.$^4$ .............................................. A61K 31/54
[52] U.S. Cl. .................................... 514/222; 514/913
[58] Field of Search ......................................... 514/222

[56] References Cited

U.S. PATENT DOCUMENTS

| | | | |
|---|---|---|---|
| 4,311,697 | 1/1982 | Krapcho | 514/222 |
| 4,431,644 | 2/1984 | Smith et al. | 544/13 |
| 4,442,089 | 4/1984 | Horovitz | 424/177 |
| 4,468,396 | 8/1984 | Magatti | 544/13 |

Primary Examiner—Douglas W. Robinson
Attorney, Agent, or Firm—James R. Nelson; Stephen I. Miller; Anita W. Magatti

[57] ABSTRACT

Pharmaceutical compositions and a method for reducing intraocular pressure by topically applying a carboxyalkyl dipeptide are disclosed.

10 Claims, No Drawings

ANTIGLAUCOMA AGENTS

This application is a continuation-in-part of Ser. No. 653,186, filed Sept. 24, 1984, now U.S. Pat. No. 4,556,655.

The present invention relates to ophthalmological pharmaceutical compositions comprising carboxyalkyl dipeptides joined through a sulfonamido group to a benzothiadiazinyl sulfonylphenyl moiety and to a method for using said composition in the treatment of glaucoma.

BACKGROUND OF THE INVENTION

Glaucoma is an ocular disease complex associated with an elevated pressure within the eye (i.e., intraocular pressure, IOP). As a result of the elevated IOP, damage to the optic nerve head resulting in irreversible loss of visual function may ensue. Untreated, this condition may eventually lead to blindness.

Ocular hypertension, i.e., the condition of elevated intraocular pressure without optic nerve head damage or characteristic glaucomatous visual field loss, is now believed by the majority of ophthalmologists to represent the earliest phase in the onset of glaucoma.

A number of the drugs presently employed to treat glaucoma are not entirely satisfactory. particularly in the earliest course of the disease when the side effects they produce are often worse than the symptoms of the disease.

Epinephrine, used as a topical solution, must be utilized cautiously in patients with high blood pressure, diabetes, hyperthyroidism and cerebral artereosclerosis due to the possibility of systemic action.

Timolol, a clinically utilized, topically applied agent for lowering intraocular pressure, must be used with caution in patients in whom beta-adrenergic blockade may be undesirable. Systemic absorption of topically administered timolol and systemic beta-blockade are responsible for the contraindication of timolol therapy for glaucoma in patients with compromised pulmonary function and in patients who cannot tolerate its systemic cardiovascular action.

Pilocarpine, a topical drug, although considered systemically harmless and quite effective, may cause considerable local difficulties. Pupil constriction causes the eye to lose its ability to adapt from light to dark. Accomodation may become stimulated so that the patient's refraction is sometimes incorrect and vision becomes blurred. The drug itself may cause a local vasodilation and red eyes. Irritation is common.

Carbonic anhydrase inhibitors have been used systemically but they have a number of disadvantages. While effective in lowering intraocular pressure, they often cause a numbness and tingling, gastrointestinal upsets and, frequently, depression, lethargy, a loss of appetite, and general malaise. European Patent Application No. 81400326.5, Publication number 36,351 attempts to overcome these difficulties by the topical administration of an alkali metal salt of a carbonic anhydrase inhibitor.

The present invention provides a new method for reducing and controlling the elevated intraocular pressure associated with glaucoma.

SUMMARY OF THE INVENTION

The invention sought to be patented in its pharmaceutical composition aspect is a topical ophthalmologically acceptable composition useful for reducing and controlling the elevated intraocular pressure associated with glaucoma which comprises an intraocular pressure reducing effective amount of a compound comprising a carboxyalkyl dipeptide joined through a sulfonamido group to a benzothiadiazinyl or sulfonylphenyl moiety as described below in combination with an ophthalmologically acceptable carrier for topical use.

The invention sought to be patented in its pharmaceutical method aspect is a method for reducing and controlling the elevated intraocular pressure associated with glaucoma in a human which method comprises administering to said human an effective amount of the above-defined pharmaceutical composition.

The compounds contemplated for use in the compositions of this invention have the following structural formula:

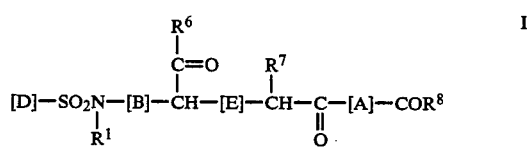

and the pharmaceutically acceptable salts thereof, wherein:

A is

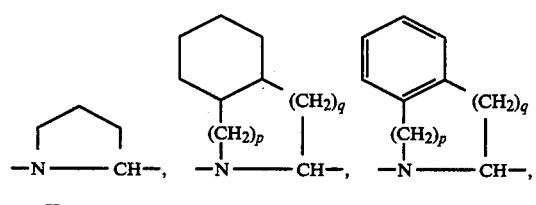

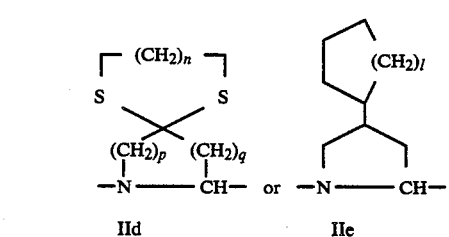

l is 1 or 2;
n is 0 or 1;
p and q are 0, 1 or 2, provided that in structures IIb and IIc the sum of p and q is 1 or 2, and that in formula IId, p is not 0;
B is -[J]-[L]-[M]-;
D is

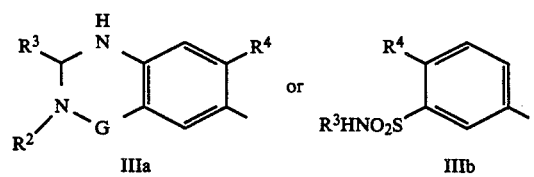

E is —NH—, —O—, —S—, or —CH$_2$—;
G is

or —SO$_2$—;

J is —(CH$_2$)$_s$— or —((CH$_2$)$_t$—W)—;

L is a chemical bond, cis- or trans-lower alkene, lower alkyne, -Z-aryl-, -aryl-Z-, -Z-cycloalkyl-, or -cycloalkyl-Z-, wherein aryl is

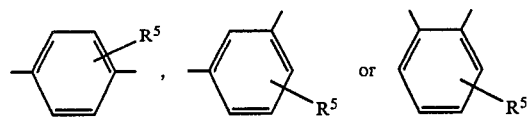

and cycloalkyl is

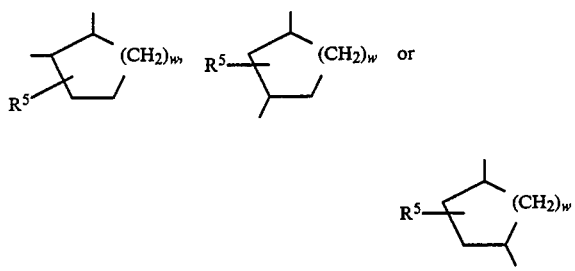

wherein w is 1, 2 or 3;

M is —(CH$_2$)$_u$—or —((CH$_2$)$_t$—X—(CH$_2$)$_v$)—;

W is

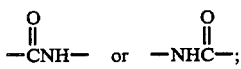

X and Z are independently a chemical bond, —NR$^9$—, —O—, —S—,

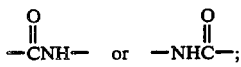

s, u and v are independently 0-5;

t is 1-5;

R$^1$, R$^2$ and R$^9$ are independently hydrogen, lower alkyl or lower acyl;

R$^3$ is hydrogen, lower alkyl, halo- and dihaloloweralkyl, trifluoroethylthiomethyl, phenylloweralkyl, (cycloalkyl)lower alkyl, aminomethyl, lower alkylaminomethyl, phenylloweralkylaminomethyl,(cycloalkyl)loweralkylaminomethyl, loweralkylthiomethyl or haloloweralkylthiomethyl;

R$^4$ is chlorine or CF$_3$;

R$^5$ is hydrogen, halogen, lower alkyl, lower acyl, lower alkoxy, haloloweralkyl or phenylloweralkyl;

R$^7$ is hydrogen, lower alkyl or aminoloweralkyl;

R$^6$ and R$^8$ are independently hydroxy, alkoxy having from 1 to 8 carbon atoms, benzyl, allyl, R$^{10}$—Q$_r$—(CH$_2$)$_m$—O—, wherein Q is oxygen or sulfur, r is 0 or 1 and m is 2 to 4,

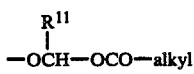

wherein the alkyl has from 3 to 8 carbon atoms,

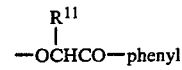

wherein the phenyl may be substituted with group T defined below, 1-glyceryl,

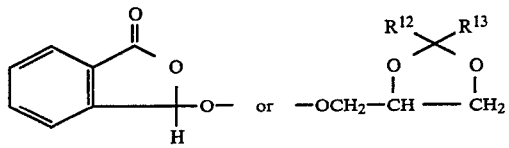

R$^{10}$ is phenyl, substituted phenyl wherein the substituents are chosen from group T, 1-naphthyl or 2-naphthyl;

T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;

R$^{11}$ is hydrogen or alkyl having from 1 to 8 carbon atoms;

R$^{12}$ is hydrogen, lower alkyl, unsubstituted or substituted phenyl and substituted or unsubstituted phenyl lower alkyl wherein phenyl may be substituted by group T;

R$^{13}$ is hydrogen or lower alkyl;

provided that if L is alkene or alkyne, J is —(CH$_2$)$_s$— wherein s is 1-5; provided that if L is -Z-aryl- or -Z-cycloalkyl-, J is —(CH$_2$)$_s$— wherein s is 2-5; provided that if L is alkene, alkyne, -aryl-Z- or -cycloalkyl-Z-, M is —(CH$_2$)$_u$— wherein u is 1-5; provided that if s and u are each zero, L is aryl or cycloalkyl (i.e. Z is a bond); and provided that if s and v are each zero, L is aryl or cycloalkyl (i.e. Z is a bond);

with the further provision that when D is of formula IIIb and R$^1$ is hydrogen, B is not —(CH$_2$)$_4$—; and that when D is of formula IIIb and R$^1$ is hydrogen or lower alkyl, B is not —(CH$_2$)$_s$—aryl—(CH$_2$)$_t$—X—(CH$_2$)$_v$— wherein s is 0 or 1, t is 1, v is 0 to 2 and X is a bond, —O—, or —S—.

When A is formula IIb or IIc, the preferred sum of p and q is 1; when A is of formula IId, preferred of p and q is 1; when A is of formula IId, preferred values for each of p and q are 1. Compounds wherein A is IIa or IIb wherein p is 0 and q is 1, and IId wherein p and q are each 1 and n is zero are preferred.

Also preferred are compounds wherein D is of formula IIIa, with compounds wherein R$^4$ is chlorine and G is —SO$_2$— being more preferred. Another group of preferred compounds are those wherein D is of formula IIIa, R$^4$ is chlorine, G is —SO$_2$—, R$^2$ is hydrogen and R$^3$ in phenylethyl, (cyclopentyl)methyl, chloromethyl, dichloromethyl, butyl, pentyl, or trifluoroethylthiomethyl.

Also preferred are compounds wherein B is

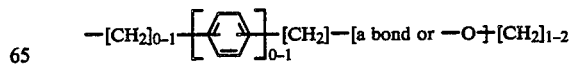

i.e., compounds wherein J is —(CH$_2$)$_s$— and s is 0-1, L is a bond or -Z-aryl- wherein Z is a bond, and M is —((CH₂)ₜ—X—(CH₂)ᵥ), wherein t is 1, v is 1-2, and X is a bond or —O—.

A preferred group for E is —NH—.

Another group of preferred compounds are those wherein R⁷ is hydrogen, methyl or aminobutyl. Still another group of preferred compounds are those wherein R⁶ and R⁸ are hydroxy.

As used herein, "lower alkyl" means straight or branched chain hydrocarbon radicals of from 1 to 6 carbons, e.g. methyl, ethyl, propyl, isopropyl, butyl, t-butyl, pentyl and hexyl. Similarly, "lower alkoxy" means straight or branched alkoxy radicals having from 1 to 6 carbon atoms, e.g. methoxy, ethoxy, propoxy, butoxy, iso-butoxy, pentoxy and hexyloxy. "Halogen" means fluorine, chlorine and bromine. "Lower acyl" means organic radicals obtained by removing the hydroxyl group from the corresponding carboxylic acid of from 1 to 6 carbons, e.g. formyl, acetyl, propionyl and butyryl. "Lower alkene" means unsaturated hydrocarbon radicals of from 2 to 6 carbon atoms having one double bond, e.g. vinylene propenyl, butenyl, pentenyl and hexenyl, wherein the double bond may be present anywhere in the chain, e.g. 1-or 2-propenyl, 1-, 2- or 3-butenyl. Similarly, "lower alkyne" means a hydrocarbon radical of from 2 to 6 carbon atoms having one triple bond, e.g. ethynylene, propynyl, butynyl, pentynyl and hexynyl, wherein the triple bond may be present anywhere in the chain, e.g. 1- or 2-propynyl, 1-, 2- or 3-butynyl.

Compounds of the instant invention include various stereoisomers. Preferred stereoisomers are those in which the absolute configuration at carbon atoms adjacent to both a nitrogen and a carbonyl group corresponds most closely to the absolute configuration of L-amino acids.

Preferred examples of compounds of formula I are as follows:

1-[2-(S)-[[1-(S)-carboxy-2-[4-[[[6-chloro-3-(chloromethyl)-3,4-dihydro-2H-1,2,4-benzothiadiazin-7-yl]sulfonylamino]methyl]phenylmethoxy]ethyl]-amino]-1-oxopropyl]-[2S-(2α, 3aα, 7aα)]-octahydro-1H-indole-2-carboxylic acid, S,S-dioxide, 1-[2-(S)-[[1-(S)-carboxy-2-[4-[[[6-chloro-3-(chloromethyl)-3,4-dihydro-2H-1,2,4-benzothiadiazin-7-yl]sulfonylamino]methyl]phenylmethoxy]ethyl]-(S)-alanyl-(S)-proline,S,S-dioxide, 1-[2-(S)-[[1-(S)-carboxy-3-[4-[[[6-chloro-3-(chloromethyl)-3,4-dihydro-2H-1,2,4-benzothiadiazin-7-yl]sulfonylamino]methyl]phenyl]propyl]amino]-1-oxopropyl]-[2S-(2α, 3aα, 7aα)]-octahydro-1H-indole-2-carboxylic acid, S,S-dioxide, N-[1-(S)-carboxy-3-[4-[[[6-chloro-3-(chloromethyl)-3,4-dihydro-2H-1,2,4-benzothiadiazin-7-yl]-sulfonylamino]methyl]phenyl]propyl]-(S)-alanyl-(S)-proline, S,S-dioxide, N-[1-(S)-carboxy-4-[4-[[[6-chloro-3-(chloromethyl)-3,4-dihydro-2H-1,2,4-benzothiadiazin-7-yl]sulfonylamino]methyl]phenyl]butyl]-(S)-alanyl-(S)-proline, S,S-dioxide, 7-N-[2-(S)-[[1-(S)-carboxy-3-[4-[[[6-chloro-3-(chloromethyl)-3,4-dihydro-2H-1,2,4-benzothiadiazin-7-yl]sulfonylamino]methyl]phenyl]propyl]amino]-1-oxopropyl]-1,4-dithia-7-azaspiro [4.4]nonane-8-(S)-carboxylic acid, S,S-dioxide, N-[1-(S)-carboxy-5-[6-chloro-3-(chloromethyl)-3,4-dihydro-2H-1,2,4-benzothiadiazin-7-yl]sulfonylamino]pentyl-(S)-alanyl-(S)-proline, S,S-dioxide, 1-[2-(S)-[[1-(S)-carboxy-5-[[-6-chloro-3-(chloromethyl)-3,4-dihydro-2H-1,2,4-benzothiadiazin-7-yl]sulfonylamino]pentyl]amino]-1-oxopropyl]-[2S-(2α, 3aα, 7aα)]-octahydro-1H-indole-2-carboxylic acid, S,S-dioxide, and the 3-(dichloromethyl)-,3-(cyclopentylmethyl)-,3-(2-phenylethyl)-, 3-(butyl)-,3-(pentyl)-, and 3-(trifluoroethylthiomethyl)-1,2,4-benzothiazinyl analogues thereof.

The compounds of this invention form salts with various inorganic and organic acids and bases which are also within the scope of the invention. Such salts include ammonium salts, alkali metal salts, e.g. calcium and magnesium salts. Salts with organic bases may be prepared, e.g., N-methylglucamine, lysine and arginine, as well as salts with organic and inorganic acids, e.g., HCl, HBr, H₂SO₄, H₃PO₄, methanesulfonic acid, toluenesulfonic acid, maleic acid, fumaric acid and camphorsulfonic acid. The non-toxic pharmaceutically acceptable salts are preferred, although other salts are also useful, e.g., in isolating or purifying the product. The acid salts (e.g. HCl and maleate) are preferred, especially the hydrochloride.

The salts may be formed by conventional means, as by reacting the free acid or base forms of the product with one or more equivalents of the appropriate base or acid in a solvent or medium in which the salt is insoluble, or in a solvent such as water which is then removed in vacuo, or by exchanging the cations of an existing salt for another cation on a suitable ion exchange resin.

Compounds of formula I may be prepared by several routes using methods known in the art.

For example, compounds of formula I can be prepared by condensing an acid of formula IV (or its hydrochloride salt) with an amino acid derivative of formula V:

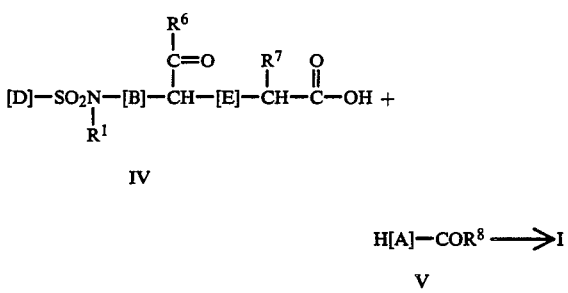

H[A]—COR⁸ ⟶ I

V wherein R¹, R⁶, R⁷, R⁸, D, B, E and A are as defined above. The reaction is carried out in an inert solvent such as dimethylformamide (DMF) in the presence a condensing agent such as 1-(3-dimethylaminopropyl)-3-ethyl carbodiimide hydrochloride (DEC) and 1-hydroxybenzotriazole, and where the compound of formula IV is a salt in the presence of a base such as triethylamine. The reaction is preferably carried out in an inert atomsphere at a temperature of 0°-25° C.

Compounds of formula V are known in the art, or may be prepared by methods well known to those skilled in the art.

Compounds of formula IV may be prepared for example from the reaction of a sulfonyl chloride of formula VI and an amine of formula VII:

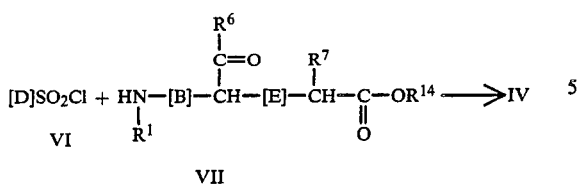

wherein D, B, E, $R^1$, $R^6$ and $R^7$ are as defined above and $R^{14}$ is a readily removable ester protecting group such as t-butyl, benzyl or trimethylsilylethyl. The reaction is carried out at 0°–5° C. in a solvent such as tetrahydrofuran (THF).

Compounds of formula VI may be prepared from known starting materials using procedures well known in the art. For example, when D is of the formula IIIa wherein G is $SO_2$ and $R^3$ is phenylethyl, the sulfonyl chlorides of formula VI may be obtained by reacting a disulfonyl chloride of formula VIII with aqueous ammonia at low temperature (dry-ice-acetone bath) in a solvent such as 1,2-dimethoxyethane (DME) in the presence of a base such as triethylamine to obtain a sulfonamide of formula IX, followed by reaction of the sulfonamide with phenyl propanal in a solvent such as DME and in the presence of an acid such as p-toluenesulfonic acid:

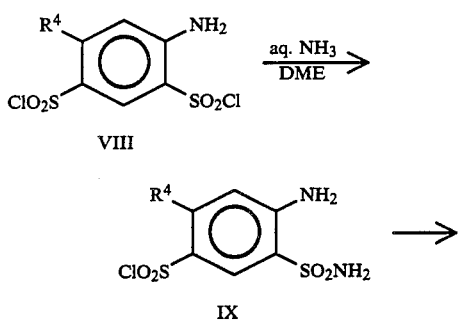

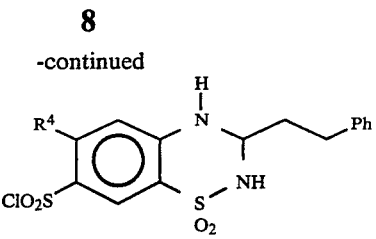

(wherein $R^2$ = H, $R^3$ = phenylethyl, $G_1$ = $-SO_2-$)

Similarly, when D is of formula IIIb, the sulfonyl chlorides of formula VI may be obtained by well known procedures. A typical reaction scheme follows:

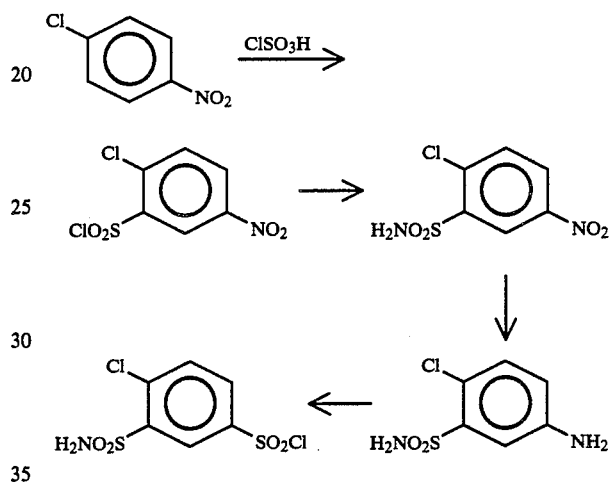

Compounds of formula VII are prepared from known starting materials using methods known in the art. A typical reaction scheme is shown below for compounds of formula VIIb, wherein $R^1$ is hydrogen, $R^6$ is lower alkyl, $R^7$ is methyl, J is $-(CH_2)-$, L is phenyl, M is $-CH_2-O-CH_2-$, E is $-NH-$, and $R^{14}$ is as defined above:

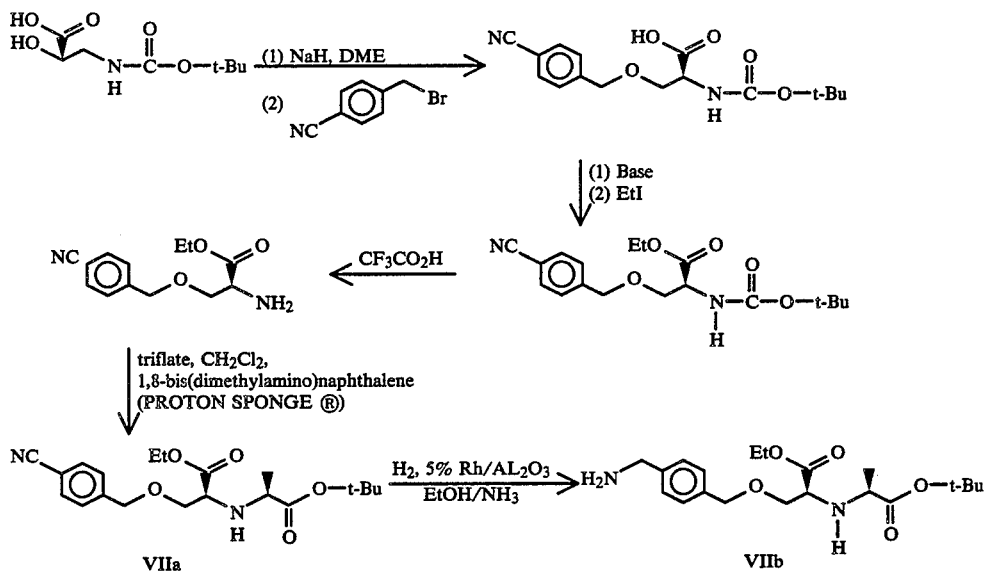

Details of the above typical reaction scheme are disclosed in Example 1, Parts A–E.

In the above reaction scheme, the triflate reagent, i.e. t-butyl 2(S)-(trifluoromethanesulfonyloxy)propionate, reacts by nucleophillic displacment with the α-aminoacid ester to give a high yield of the corresponding specific diastereomer of the resulting monoamino dicarboxylic acid ester. Compounds of formula VIId, wherein M is (CH$_2$)$_2$ and R$^1$, R$^6$, R$^7$, R$^{14}$, J, L and E are as described above for formula VIIb, may be prepared as follows:

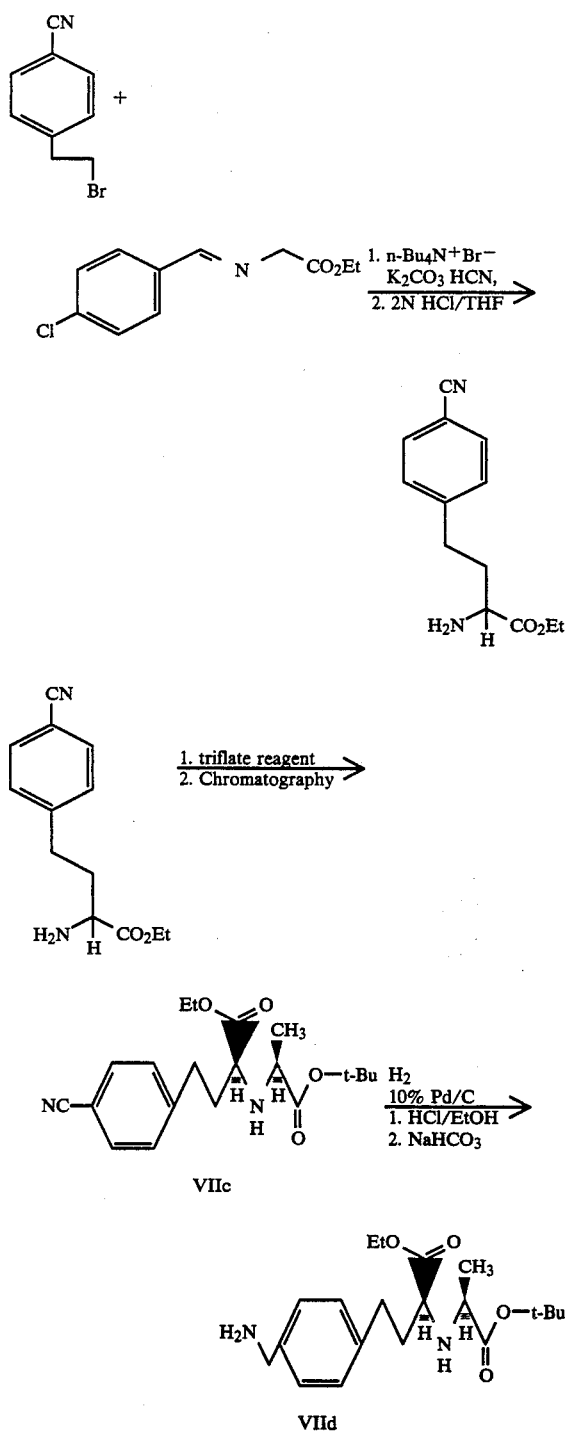

The above reaction scheme is exemplified In Parts A-C of Example 3.

A typical reaction scheme for the preparation of compounds of formula VIIf wherein L is a bond, J is —(CH$_2$)$_s$—and M is —(CH$_2$)$_u$)— wherein the sum of s and u is 4, and R$^1$, R$^6$, R$^7$, R$^{14}$ and E are as described above for formula VIIb is as follows:

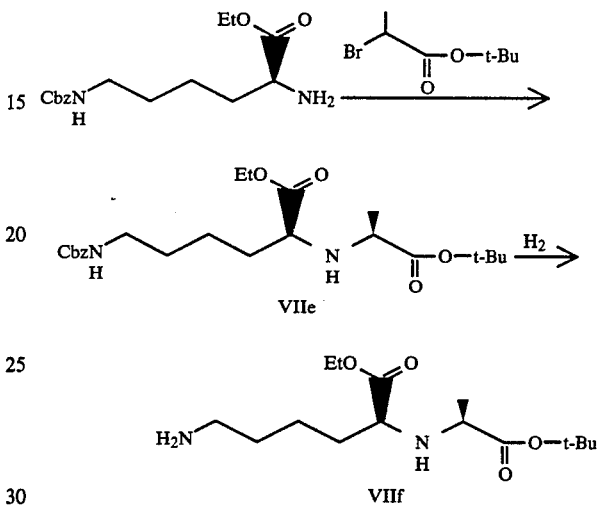

Example 5 provides details of this procedure.

Alternatively, intermediates of formulae VIIa or VIIc may be used to prepare compounds of formula I as follows: The R$^{14}$ protecting groups (e.g. t-butoxycarbonyl) of compounds of formulae VIIa or VIIc may be removed, e.g. by trifluoroacetic acid, and the nitrile reacted with an amino acid derivative of formula V under the conditions described on page 7. The resulting nitrile can then be reduced to the corresponding amine, e.g., by hydrogenation, which amine can then in turn be coupled to a sulfonyl chloride of formula VI by conventional methods. Similarly, intermediates of formula VIIe (i.e., compounds of formula VII wherein B is alkyl) may be deprotected at the carboxylic acid group and condensed with the amino acid derivative of formula V as described above, then deprotected at the amino group, e.g. by hydrogenation, and the resultant amine reacted with a sulfonyl chloride of formula VI by conventional methods.

Another method for preparing compounds of formula IV is that exemplified below for preparing compounds wherein D is of formula IIIa wherein G is —SO$_2$—, J is —CH$_2$—, L is —aryl-Z— wherein aryl is phenyl and Z is

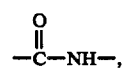

M is —CH$_2$—, E is —NH—, R$^1$ is hydrogen, R$^6$ is ethyl, R$^7$ is methyl, and R$^2$, R$^3$ and R$^4$ are as defined above:

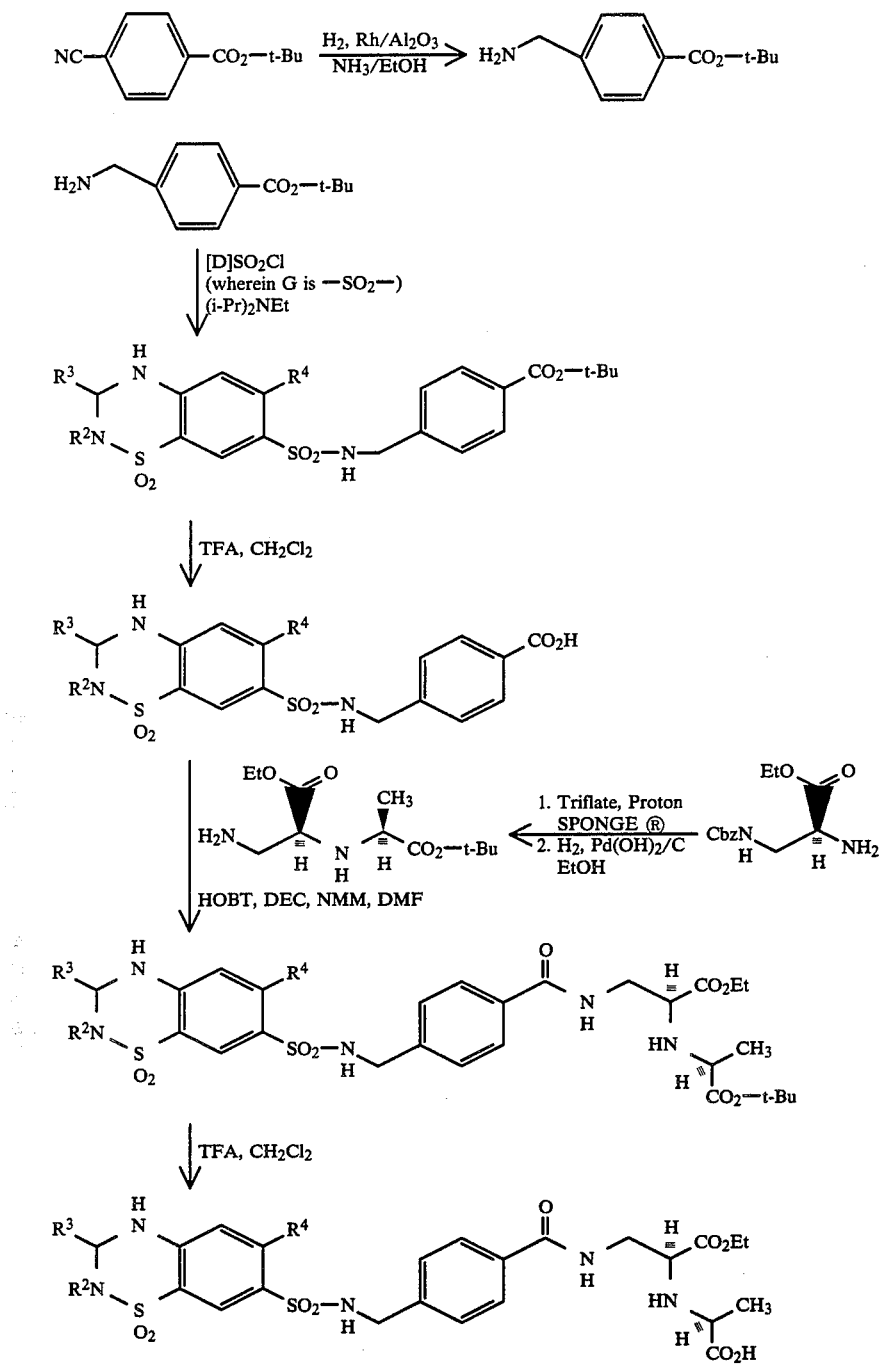

Example 7 incorporates the above procedure.

The known coupling methods above include amino group protection during the coupling reaction, for example with protecting groups such as N-formyl, N-t-butoxycarbonyl (t-Boc) and N-carbobenzyloxy (Cbz) groups, followed by their removal to yield compounds of formula I. Furthermore, the $COR^8$ function wherein $R^8$ is OH may be protected by removable ester groups such as benzyl, ethyl, t-butyl, trimethylsilylethyl and the like.

The more complex esters at $R^6$ (i.e., $R^6$ is other than hydroxy or alkoxy) are most conveniently prepared by esterifying compounds compounds of formula I wherein $R^6$ is hydroxy and $R^8$ is a protected hydroxy, e.g. benzyloxy, with the appropriate reagents, e.g. chloromethyl pivalate in the presence of base, to obtain the corresponding pivaloyloxymethyl ester; the benzyl group is then removed by conventional means, e.g. catalytic hydrogenation.

The following procedures and examples further illustrate the preparation of compounds of this invention.

PREPARATION 1 t-BUTYL 2(S)-(TRIFLUOROMETHANESULFONYLOXY)-PROPRIONATE (Triflate Reagent)

A. Add 2(S)-(p-toluenesulfonyloxy)propionic acid (4.4 g) to a cold solution of 10ml of isobutylene and 0.4 ml of concentrated sulfuric acid in 30 ml of methylene chloride in a pressure vessel, seal, and agitate at room temperature for 48 hours. Pour into 50 ml of 15% sodium carbonate solution, dry over magnesium sulfate and concentrate to obtain t-butyl 2(S)-(p-toluenesulfonyloxy)propionate as an oil (NMR $\delta$1.37). Distilled material (Kugelrohr, 120°) has $[\alpha]D^{26} = -45.9°$ (EtOH, c=1).

B. Combine the product of part A (100 g) with acetic acid (40.0 g) and triethylamine (67.2 g) in 200 ml of dry DMF. Heat at 65° for 20 hours. Partition with 2l each ether and water, and wash the ether with citric acid, then with dilute sodium bicarbonate soultion. Dry and concentrate the ether solution to obtain t-butyl 2(R)-acetoxypropionate as a colorless liquid, bp 50° C./0.1 mm.

C. Combine the product of part B (62,6 g) with ethylenediamine (11.6 g) and heat at 70° for 24 hours. allow to cool, add 300 ml ether and filter. Wash the ether with water, 10% citric acid, and then with sodium bicarbonate solution. Dry and concentrate the ether solution to leave a colorless oil. Crystallize from hexane at $-20°$ to give t-butyl 2(R)-hydroxypropionate as white needles, m.p. 41°-2° C.

D. Combine the product of part C (10 g) with pyridine (6 ml) in 100 ml methylene chloride. Cool to $-70°$ C., and add dropwise over a period of about 45 minutes a solution of trifluoromethanesulfonic anhydride (13.5 g) in 20 ml methylene chloride, maintaining the temperature below $-15°$ C. Stir at $-20°$ C. for 30 min. Add ether and wash successively with water, 4 of aq HCl, sat'd NaHCO$_3$ and brine. Dry and concentrate the organic layer to obtain the title compound.

PREPARATION 2

6-CHLORO-3,4-DIHYDRO-3-(2-PHENYLETHYL)-2H-1,2,4-BENZOTHIADIAZINE-7-SULFONYL CHLORIDE 1,1-DIOXIDE

A. Dissolve 5 g 2-chloroaniline-3,5-disulphonyl chloride in 20 ml DME, cool to in a dry-ice/acetone both and add 2 ml triethylamine. Add dropwise 25% ammonium hydroxide in water (1 ml) in DME (4 ml), stir at in a dry-ice acetone bath for 1 hour, allow to warm to room temperature, and stir for 90 min. Dilute the resultant reaction mixture with ethyl acetate, wash with 4% aq HCl, water and brine, dry over MgSO$_4$ and evaporate to obtain a solid residue.

B. Combine 13.6 g of the sulfonamide prepared in Step A, 6.57 g phenyl propanal, 25 ml DME and 20 mg p-tolulenesulfonic acid and stir at room temperature under N$_2$ for 3 hours. Evaporate the solvent, dissolve the resultant . residue in 250 ml ethyl acetate, wash with 100 ml sat'd aq. NaHCO$_3$, and 100 ml brine, then dry over MgSO$_4$, filter and evaporate the solvent to obtain the crude title compound. Purify the crude residue by precipitation in CH$_2$Cl$_2$; mp. 167.0°-167.5° C.

PREPARTION 3

CIS,SYN-OCTAHYDROINDOLE-2(S)-CARBOXYLIC ACID, t-BUTYL ESTER

A. Dissolve the product of Preparation 4 (77 g) in absolute ethanol (900 ml), add 5% Pd/C (10 g) and hydrogenate at room temperature at an initial pressure of 60 p.s.i. After 3 hours, filter off the catalyst and wash with hot methanol. Evaporate the combined filtrate and wash in vacuo, triturate the resultant residue in ethanol (100 ml), chill the solution, then filter and air dry the resultant precipitate to obtain a residue, m.p. 269°-270° C.

B. Suspend the product of Part A in dioxane (400 ml) and conc. H$_2$SO$_4$ (40 ml), add isobutylene (300 ml) and shake in a Parr shaker for 28 hours. Pour the resultant reaction mixture into 50% aqueous NaOH (150 ml) in 500 ml ice water and extract with ethyl ether (3$\times$500 ml). Wash the combined organic extracts with water, then brine. Dry the the organic layer over Na$_2$SO$_4$ and evaporate the solvent to obtain the title compound.

PREPARATION 4

CIS,SYN-OCTAHYDROINDOLE-2(S)-CARBOXYLIC ACID BENZYL ESTER

A. Dissolve 27.0 g of ethyl indole-2-carboxylate in 250 ml of trifluoroacetic acid. Add 2.05 g of platinium oxide, hydrogenate the mixture at 50 lb/in$^2$ at room temperature. Filter the mixture and concentrate the filtrate in vacuo to give a residue. Suspend the residue in ether and treat with cold dilute sodium hydroxide solution. Dry the organic layer over magnesium sulfate and concentrate it to give ethyl octahydroindole-2-carboxylate, a pale yellow oil.

B. Dissolve 116 g 10-d-camphorsulfonic acid in 1 liter of warm ethyl acetate and add a soultion of 86 g of the product of part A in 1 liter of ethyl acetate. Allow the mixture to crystallize, heat to reflux, cool to room temperature, and filter. Recrystallize the filter cake from a mixture of 500 ml isopropanol and 1800 ml ethyl acetate, filter and dry the crystals to obtain 2-(S)-carboethoxy-cis,syn-octahydroindole, d-10-camphorsulfonate, m.p. 192°-193° C.

C. Heat the product of Part B (107.6 g) and d-10-camphorsulfonic acid (6.35 g) in benzyl alcohol (270 ml) at 105° C. under vacuum for 6 hours or until TLC (silica, elute neutralize sample with ethyl ether) indicates reaction is complete. Pour the resultant residue into ethyl ether, seed and stir to obtain a precipitate. Filter the precipitate, wash with ethyl ether (2$\times$500 ml) and dry the resultant residue under vacuum to obtain 2-(S)-benzyloxy-cis, syn-octahydro-indole, d-10-camphorsulfonate, m.p. 114°-118° C.

D. Suspend the product of Part C (150 g) in ethyl ether (1500 ml), add 1N aqueous NaOH (300 ml) and stir until the solid dissolves. Separate the organic layer and wash the aqueous layer with ethyl ether (2$\times$200 ml). Combine the organic layer, wash with brine, dry over Na$_2$SO$_4$ and evaporate the solvent to obtain the title compound.

PREPARATION 5

6-CHLORO-3,4-DIHYDRO-3-(CHLOROMETHYL)-2H-1,2,4-BENZOTHIADIAZINE-7-SULFONYL CHLORIDE 1,1-DIOXIDE

A. Dissolve the sulfonamide prepared in Part A of Preparation 2 (20 g) in dry DME (100 ml), add chloroacetaldehyde dimethyl acetal (10 ml) and p-toluenesulfonic acid and reflux for 3 hours or until TLC (silica, 3% ethyl acetate in $CH_2Cl_2$) indicates reaction is complete. Evaporate the solvent, dissolve the resultant residue in ethyl acetate, wash with saturated $NaHCO_3$, then brine and concentrate to half volume. Refrigerate overnight, filter the resultant precipitate, wash in hexane, filter and dry to obtain the title compound.

EXAMPLE 1

1-[2-(S)-[[1-(S)-CARBOETHOXY-2-[4-[[[6-CHLORO-3,4-DIHYDRO-3-(2-PHENYLETHYL)-2H-1,2,4-BENZOTHIADIAZIN-7-YL]SULFONYLAMINO]METHYL]PHENYLMETHOXY]ETHYL]AMINO]-1-OXOPROPYL]-[2S-[2α, 3aα, 7aα)]-OCTAHYDRO-1H-INDOLE-2-CARBOXYLIC ACID, S,S-DIOXIDE

A. To 10.4 g NaH (50% in mineral oil, washed with hexane) in 50 ml DMF at 0°-5° C., add dropwise over a 1 hour period 20 g of N-a-t-butoxycarbonyl-L-serine in 350 ml DMF. Stir at room temperature for 1 hour, then at 45° for 1 hour. Cool the reaction mixture to 0°-5° C. and add dropwise over 30 minutes 21.3 g of p-cyanobenzylbromide in 100 ml DMF. Stir at 0° C. for 80 minutes, add 30 ml water, stir and filter. Concentrate the filtrate and partition between ethyl acetate and sat'd. aq. $NaHCO_3/H_2O$. Wash the aqueous phase with ethyl acetate, adjust to pH 7.5 with 6N HCl and concentrate to approximately 100 mls.

B. To the product of Step A, add 60 ml methanol, 40 ml ethyliodide, and 4 g $NaHCO_3$. Stir under a nitrogen atmosphere for 72 hours, evaporate the solvent in vacuo and partition the residue between 800 ml ethyl acetate and 800 ml water. Separate the organic layer, and extract the aqueous layer with ethyl acetate; combine the organic extracts, wash with brine, dry over $MgSO_4$, filter and evaporate the solvent. Purify the resultant residue by High Pressure Liquid Chromatography (HPLC) using 2 Prep 500 cartridges and eluting with 21% ethyl acetate in hexane. Combine the desired fractions and evaporate the solvent to obtain a residue. FAB mass spec m/e=349 (M+H).

C. Cool 2 g of the product of Step B to 0°-5° C. and add dropwise 25 ml trifluoroacetic acid. Let stand until TLC (silica, elute with hexane:ethyl acetate) indicates no starting material is left. Add ethyl acetate, then evaporate the solvent in vacuo. Dissolve the resultant residue in ethyl ether, and wash with 1N aqueous NaOH; backwash the aqueous phase with ether, combine the ethereal extracts, dry over $K_2CO_3$ and evaporate the solvent to obtain a residue.

D. Cool 1.6 g triflate reagent (Preparation 1) in 10 ml $CH_2Cl_2$ to 0° C. Add dropwise 1.1 g of the product of Step C and 1.2 g of PROTON SPONGE® (1,8-bis(-dimethylamino)naphthalene, Aldrich Chemical Co., Milwaukee, WI) in 20 ml $CH_2Cl_2$. Monitor reaction by TLC, adding 1,8-bis(dimethylamino)naphthalene and triflate reagent as necessary. Filter the resultant precipitate with the aid of ethyl acetate, evaporate the solvent, and purify the resultant residue by column chromatography, eluting with 30% ethyl acetate in hexane. FAB mass spec m/e=377 (M+H).

E. Dissolve 2.5 g of the product of Step D in 50 ml ethanol saturated with $NH_3$, add 1.25 g 5% $Rh/Al_2O_3$ and hydrogenate at 60 psi for 4 hours. Filter the resultant mixture through celite with the aid of ethanol, then evaporate the solvent in vacuo to obtain a residue.

F. Cool to 0° C. 2.5 g of the product of Step E in 25 ml dry THF and add dropwise 3.3 g 6-chloro-3,4-dihydro-3-(2-phenylethyl)-2H-1,2,4-benzothiadiazine-7-sulfonyl chloride 1,1-dioxide in 20 ml dry THF. Stir at 0° C. for 1 hour, then add 0.6 ml N,N-diisopropylethylamine and stir at room temperature for 2 hours. (Reaction may be monitored by TLC [silica; elute with hexane: ethyl acetate]). Add the reaction mixture to ethyl acetate, wash with 4% aq. HCl, sat'd $NaHCO_3$ and brine, then dry over $MgSO_4$ and evaporate the solvent in vacuo. Purify the resultant residue by HPLC: dissolve the residue in acetone:ethyl acetate:hexane (20:35:45) and separate on 2 Prep 500 cartridges using acetone:ethyl acetate:hexane (5.5:36.5:58) as mobile phase. Monitor eluent by TLC (silica; elute with acetone:ethyl acetate:hexane [6:39:55]), combine the desired fractions and evaporate the solvent in vacuo to obtain a residue. FAB mass spec m/e=766 (M+H).

G. Stir 2.9 g of the t-butyl ester of Step F in 40 ml HCl/dioxane overnight; pass nitrogen through the solution to evaporate the solvent and obtain the free acid.

H. Dissolve 2.9 g of the product of Step G in 6 ml DMF, add 1.1 g cis,syn-octahydro-1H-indole-2(S)carboxylic acid, t-butyl ester and 700 mg 1-hydroxybenzotriazole. Cool to 0° C., add 0.7 ml triethylamine and 900 mg 1-(3-dimethylaminopropyl)-3-ethyl carbodiimide hydrochloride and stir overnight. Evaporate the solvent in vacuo, take up the residue in ethyl acetate, and wash with water, 4% aq. HCl, sat'd aq. $NaHCO_3$, and brine. Dry the organic layer over $MgSO_4$, filter and evaporate to obtain a residue.

Purify said residue by HPLC using 2 Prep 500 cartridges and methanol:ethyl acetate:hexane (5.25:36:58.75) as mobile phase (residue dissolved in methanol:ethyl acetate:hexane [10:35:55]). Combine the desired fractions as determined by TLC and evaporate the solvent. Rechromatograph the resultant residue by HPLC using acetone:ethylacetate:hexane (10:40:50) as mobile phase, combining the desired fractions and evaporating the solvent to yield the title compound as a t-butyl ester. FAB mass spec m/e=917 (M+H).

I. Stir 1.5 g of the product of Step H in 20 ml dioxane saturated with HCl overnight; pass nitrogen through the solution to evaporate the solvent. Purify the resultant residue on Dowex Ag 50 2X (H+ form), eluting with (ethanol:water [1:1]):pyridine (95:5). Combine desired fractions as determined by TLC (silica; $CH_2Cl_2$: MeOH:AcOH [90:5:3]) and evaporate the solvent to obtain the title compound. FAB mass spec m/e=861 (M+H).

EXAMPLE 2

1-[2-(S)-[[1-(S)-CARBOXY-2-[4-[[[6-CHLORO-3,4-DIHYDRO-3(2-PHENYLETHYL)-2H-1,2,4-BENZOTHIADIAZIN-7YL]SULFONYLAMINO]METHYL]PHENYLMETHOXY]ETHYL]AMINO]-1 OXOPROPYL]-[2S-(2α, 3aα, 7aα)]-OCTAHYDRO-1H-INDOLE-2-CARBOXYLIC ACID, S̄,S-DIOXIDE.

A. Treat the product of Example 1, Step G in a manner similar to that described in Example 1, Step H, first paragraph, substituting cis,syn-octahydro-1H-indole-2(S)-carboxylic acid, benzyl ester camphorsulfonate salt (see Preparation 4, Part C) for the t-butyl ester.

Purify the resultant residue by column chromatography on 100 g silica eluted with $CHCl_3$:ethyl acetate. Combine the desired fractions as determined by TLC (silica; elute with $CH_2Cl_2$:methanol:acetone [93:2:5]) and evaporate the solvent to obtain a residue. Further purify the residue on a sephadex column (350g). FAB mass spec m/e=951 (M+H).

B. Suspend 450 mg of the diester obtained in Step A in 2 ml water. Add 2 ml 1N aq. NaOH and stir overnight at room temperature. Adjust to pH 6–7 with 1N HCl, filter the resultant solid and dry under vaccum to obtain the title compound. FAB mass spec m/e=833 (M+H).

EXAMPLE 3

1-[2-(S)-[[3-[4-[[[6-CHLORO-3,4-DIHYDRO-3-(2-PHENYLETHYL)-2H-1,2,4-BENZOTHIADIAZIN-7-YL]SULFONYLAMĪNOMETHYL]PHENYL]-1-(S)-(ETHOXYCARBONYL)PROPYL]AMINO]-1OXOPROPYL]-[2S-(2α, 3aα, 7aα]-OCTAHYDRO-1H-INDOLE-2-CARBOXYLIC ACID, S,S -DIOXĪDE HYDROCHLORIDE

A. 2-Amino-4-(4-cyano)phenylbutanoic acid, ethyl ester

Reflux 2-(4-cyano)phenylethyl bromide (23 gm), the p-chlorobenzaldimine of ethyl glycinate (21 gm), tetra-n-butylammonium bromide (10 gms) and freshly ground fine potassium carbonate powder (42 gms) in acetonitrile (150 mls) with mechanical stirring under nitrogren for 12 hours.

Cool the mixture, filter off the solid and wash the filter cake with ethyl acetate (3×150 mls). Wash the combined filtrate with water (2×100 mls) and evaporate the solvent in vacuo. Stir the residue vigorously with THF (200 mls) and 2N HCl (200 mls) at room temperature for 2 hours. Wash the aqueous phase with ethyl acetate, basify with solid potassium carbonate to pH 9 and extract with ethyl acetate to give the title compound of Part A.

B. N-[1-(S)-(Ethoxycarbonyl)-3-(4-cyano)phenyl]-(S)-alanine, t-butyl ester

Slowly add the product of Part A (9 gms) and PROTON SPONGE® (17.2 gm) in dry dichloromethane (80 mls) dropwise into a stirred solution of triflate reagent (22 gm) in dry dichloromethane (40 mls) cooled in an acetone-ice bath. Stir at room temperature overnight. Filter the resultant precipitate and wash the filter cake with ethyl acetate (5×100 ml). Wash the combined filtrate with 10% citric acid (3×100 ml); sodium bicarbonate (sat'd, 2×100 ml), and saturated brine (2×100 ml). Dry the solution over potassium carbonate in the presence of triethyl amine (5 mls), and remove the solvent in vacuo. Chromatograph the resultant residue (hexane:EtOAc:$CH_2Cl_2$[8:1:1], 1% $Et_3N$; 500 gm silica gel; 230–400 mesh) to obtain the title compound of Part B.

C. N-[3-(4-Aminomethyl)phenyl-1-(S)-(ethoxycarbonyl) propyl]-(S)-alanine, t-butyl ester Hydrogenate a mixture of the product of Part B (2 g), hydrogen chloride (0.2 gm) and 10% Pd/C (0.4 gm) in absolute ethanol (100 ml) at 50 psi for 5 hours. Filter the resultant mixture through celite. Evaporate the solvent to obtain the hydrogen chloride salt of the title compound of Part C.

D. Add N-methylmorpholine (0.5 ml) to a solution of the product of Part C (1 gm) in dry THF (20 mls) cooled in acetone-ice bath (−5° C.). Add the sulfonyl chloride of Preparation 2 (1.3 gm) and stir the resulting mixture at room temperature overnight. Dilute the resultant reaction mixture with ethyl acetate (400 ml), wash with 0.5N HCl (100 ml), saturated $NaHCO_3$ (2×100 ml), and brine (2×100 ml). Dry the solution over $MgSO_4$ and remove the solvent in vacuo. Purify the resultant residue by chromatography [400 gm silica gel, 230–400 mesh; first hexane:EtOAc:$CH_2Cl_2$, 4:1:1, then hexane:EtOAc:$CH_2Cl_2$, 1:1:1] to obtain a residue.

E. Add the product of Part D (1.76 gm) to 5.5 M HCl in dioxane (50 ml) and stir the resulting mixture at room temperature overnight. Evaporate the solvent in vacuo, triturate the solid residue with ether, and remove the solvent in vacuo to obtain a residue (hydrogen chloride salt).

F. Treat the product of Part E in a manner similar to that described in Example 1, Part H, first paragraph, substituting N-methylmorpholine for triethylamine to obtain a residue. Purify the resultant residue by chromatography [400 gm silica gel 230–400 mesh; hexane:EtOAc:$CH_2Cl_2$, 1:2:1] to obtain the t-butyl ester of the title compound.

G. Stir the product of Part F (0.9 gm) in 5.5 M HCl/dioxane (40 mls) at room temperature for 2 hours. Remove the solvent in vacuo, triturate the product with ether, and dry in vacuo to obtain the title compound of Example 3.

EXAMPLE 4

1[2-(S)[[1-(S)-CARBOXY-3[4-[[[6-CHLORO-3,4-DIHYDRO-3-(2-PHENYLETHYL)-2H1,2,4-BENZOTHIADIAZIN-7-YL]SULFONYL-AMINO]METHYL]PHENYL]-PROPYL]AMINO]-1-OXO-PROPYL]-[2S-(2α, 3aα,7aα)]-OCTAHYDRO-1H-INDOLE-2-CARBOXYLIC ACID, S,S̄- DIOXIDE

Dissolve the product of Example 3 (0.85 gm) in methanol (2 mls) and cool to 0° C. under nitrogen. Add 1N sodium hydroxide (5 mls) portionwise. Refrigerate the mixture overnight. Acidify the resultant mixture with acetic acid, evaporate to dryness, and purify the residue by chromatography on a C-18 medium pressure reverse-phase column to yield the title compound of Example 4.

EXAMPLE 5

1-[[2-(S)-[5-[[6-CHLORO-3-CHLOROMETHYL-3,4-DIHYDRO-2H-1,2,4-BENZOTHIADIAZIN-7-YL]SULFONYLAMINO]-1-(S)-(ETHOXYCARBONYL)PENTYL]AMINO]-1-OXOPROPYL]-[2S-(2α,3aα,7aα)]-OCTAHYDRO-1H-INDOLE-2-CARBOXYLIC ACID, S̄,S-DIOXIDE

A. Combine N$^\epsilon$Cbz lysine, ethyl ester (30.0 g), t-butyl bromopropionate (44.78 g), triethylamine (14.8 ml) and DMF (120 ml) and stir under nitrogen at 75° C. until TLC shows no starting material present. Evaporate the solvent, dilute the resultant residue with water and extract with ethyl ether. Wash the organic layer with brine, dry over MgSO$_4$, filter and evaporate the solvent in vacuo.

Purify the resultant residue by column chromatography on 1,100 g silica gel (60-200 mesh), eluting with ether:hexane (50:50→75:50). Combine the desired fractions and evaporate the solvent in air. Further purify the resultant residue by HPLC using 2 Prep 500 cartridges and eluting with ether:hexane. Combine desired fractions, dry over MgSO$_4$ and evaporate the solvent in air to obtain a residue.

B. Combine 20% Pd(OH)$_2$/C (21.1 g) and anhydrous ethanol (25 ml) in a Parr shaker bottle, add the product of Part A (16.5 g) in ethanol (55 ml) and hydrogenate overnight under 60 p.s.i. H$_2$. Filter the resultant solution over filter paper and celite and evaporate the solvent to obtain a residue.

C. Dissolve the sulfonyl chloride prepared in Preparation 5 (2.4 g) in dry DME (15 ml). Add triethylamine (1 ml) and the product of Part B of this Example (2 g) in DMF (10 ml) and stir for 1 hour, or until TLC (silica, 10% MeOH in CH$_2$Cl$_2$) indicates no starting material is left. Add the resultant solution to ethyl acetate, wash with water, saturated NaHCO$_3$ and brine, dry over MgSO$_4$ and evaporate the solvent in vacuo. Purify the resultant residue on a Sephadex LH20 column to obtain a residue. FAB mass spec m/e=632 (M+H).

D. Treat the product of Part C in a manner similar to that described in Example 1, Part G.

E. Treat the product of Part D in a manner similar to that described in Example 1, Part H, first paragraph, substituting the camphorsulfonate salt of the benzyl ester of the octahydroindole (see Preparation 4 Part C) for the t-butyl ester.

Purify the resultant residue on a sephadex LH20 column, combine the desired fractions and evaporate the solvent. Dissolve the resultant residue in ethyl acetate, add dioxane saturated with HCl and evaporate the solvent to obtain the benzyl ester of the title compound. FAB mass spec m/e=817 (M+H).

F. Dissolve the product of Part E (600 mg) in acetic acid saturated with hydrogen bromide (6 ml). After 5 hours, evaporate the solvent and purify the resultant residue on a Sephadex LH20 column. Combine the desired fractions as determined by TLC (silica, MeOH:CH$_2$Cl$_2$:acetic acid, 10:90:4) and evaporate the solvent to obtain the title compound. FAB mass spec m/e=726 (M+H).

EXAMPLE 6

1-[[2-(S)-[1-(S)-CARBOXY-5-[[6-CHLORO-3-CHLOROMETHYL-3,4-DIHYDRO-2H-1,2,4-BENZOTHIADIAZIN-7-YL]SULFONYLAMINO]PENTYL]AMINO]-1-OXOPROPYL]-[2S-(2α,3aα,7aα)]-OCTAHYDRO-1H-INDOLE-2-CARBOXYLIC ACID, S̄, S/ -DIOXIDE

Add the product of Example 5, Part E (benzyl ester) to 1N aqueous NaOH (4 ml) and water (4 ml) and stir overnight. Add 1N HCl (4 ml) and ethanol. Charge the resultant solution to Dowex Ag 50 cation exchange resin by stirring batchwise for 20 minutes (60 ml resin, pre-washed with ethanol:water, 1:4). Prepare a column from the loaded resin, elute the column with ethanol:water (1:4) until the elute is pH 6, then elute with ethanol/water:pyridine (95:5). Combine the desired fractions as determined by TLC (silica, ethanol:water, 9:1). Further purify the resultant product on a Sephadex LH 20 column. Combine the desired fractions and evaporate the solvent to obtain the title compound. FAB mass spec m/e+698 (M+H).

EXAMPLE 7

N-[2-[[4-[[[6-CHLORO-3,4-DIHYDRO-3-(2-PHENYLETHYL)-2H-1,2,4-BENZOTHIADIAZIN-7-YL]SULFONYLAMINO]METHYL]PHENYL]-CARBONYL]AMINO-1-(S)-(ETHOXYCARBONYL)ETHYL]-(S)-ALANYL-(S)-PROLINE, S̄/ -DIOXIDE

A. Dissolve 4-cyanobenzoic acid, t-butyl ester (11.34 g) in ethanol (100 ml) saturated with anhydrous NH$_3$, add 5% Rh/Al$_2$O$_3$ (120 g) and hydrogenate in a Parr apparatus at 60 p.s.i. at room temperature for 2¾ hours. Filter the resultant solution through celite and evaporate the solvent to obtain a residue.

B. Dissolve the product of Part A (11.27 g) in dry THF (100 ml) add N,N,-diisopropylethyl amine (8.44 g) and cool to 0° C. in an ice bath. Add dropwise, slowly and with stirring, the sulfonyl chloride prepared in Preparation 2 (27.51 g) and let stand at 0° C. for 35 minutes. Remove the ice bath and stir at room temperature for 2½ hours or until TLC (silica, CH$_2$Cl$_2$:MeOH, 95:5) shows the reaction to be complete. Evaporate the solvent to obtain a residue.

C. Cool to 0° C. a solution of the product of Part B (3.00 g) in CH$_2$Cl$_2$ (25 ml) and add, slowly and with stirring, trifluoroacetic acid (25 ml). Stir for 30 minutes at 0° C., then at room temperature for 2¼ hours or until TLC (as in Part B) shows the reaction to be complete. Evaporate the solvent to obtain a residue.

D. Dissolve triflate reagent as prepared in Preparation 1 (3.31 g) in CH$_2$Cl$_2$ (75 ml) and cool to 0° C.; add, slowly and with stirring a solution of PROTON SPONGE® (4.24 g) and N-βCbz-2,3-diaminopropionate, ethyl ester (2.00 g) in CH$_2$Cl$_2$ (75 ml). Stir at 0° C. for 15 hours. Extract the solution with 10% citric acid (2x), then sat'd. NaHCO$_3$ (2x), dry the organic layer over MgSO$_4$, filter and evaporate the solvent. Purify the resultant residue by flash chromatography, eluting with CH$_2$Cl$_2$:EtOAc (88:12). Combine the desired fractions and evaporate the solvent. Dissolve the Cbz-diester (0.5 g) in ethanol (25 ml) containing 20% Pd(OH)$_2$/C (0.15 g) and hydrogenate in a Parr apparatus at 50 p.s.i. at room temperature for 1 hour. Filter the resultant solution through celite and evaporate the filtrate in vacuo.

Combine the resultant residue (0.33 g) and the product of Part C (0.59 g) in dry DMF (7 ml), cool to 0° C. and add slowly 1-hydroxybenzotriazole (0.18 g) followed by N-methyl morpholine (0.13 g), then by DEC (0.25 g). Stir the mixture for 20 min. at 0° C., then at room temperature for 16 hours or until TLC (silica, ethanol:methanol, 85:15) indicates the reaction to be complete. Dilute the reaction mixture with $CH_2Cl_2$ and extract with saturated $NaHCO_3$, then with 10% aqueous citric acid. Dry the organic layer with $MgSO_4$, filter and evaporate the solvent in vacuo to obtain a residue.

E. Dissolve the product of Part D (0.75 g) in $CH_2Cl_2$ (5 ml) and cool to 0° C. Add, slowly and with stirring, trifluoroacetic acid (5 ml) and stir at 0° C. for 30 minutes, then at room temperature for 4 hours or until TLC (silica, $CH_2Cl_2$:MeOH, 90:10) indicates no starting material is left. Evaporate the solvent.

Purify the resultant residue by ion exchange chromatography on Biorad AG50-W-X2 resin (100–200 mesh, hydrogen form) previously equilibrated in ethanol:water. Elute with ethanol:water:pyridine, combine the desired fractions and evaporate the solvent to obtain a residue.

F. Treat the product of Part E in a manner similar to that described in Example 3, Parts F and G, substituting proline, t-butyl ester for the octahydro-1H-indole to obtain the title compound.

EXAMPLE 8

N-[5-[[6-CHLORO-3,4-DIHYDRO-3-(2-PHENYLETHYL)-2H-1,2,4-BENZOTHIADIAZIN-7-YL]SULFONYLAMINO]-1-(S)-(METHOXYCARBONYL)-PENTYN-3-YL]-(S)-ALANYL-(S)-PROLINE, S/-DIOXIDE,HYDROCHLORIDE

A. Titrate a solution of diazomethane in ether into a solution of 1-amino-1-(S)-carboxy-5-(t-butoxycarbonyl amino)-3-pentyne (4 g) in ethanol (200 ml) until a yellow color remains. Evaporate the solvent to obtain 1-amino-1-(s)-methoxycarbonyl-5-(t-butoxycarbonylamino)-3-pentyne.

B. Add the product of Part A (4 g) and PROTON SPONGE ® (5 g) in dichloromethane (15 ml) dropwise to a stirred solution of triflate reagent (6.5 g) (See Preparation 1) in dichloromethane (10 ml) at −10° C. Stir the solution and slowly allow to warm to room temperature over 2 h. Filter the reaction mixture through celite, washing thoroughly with ethyl acetate. Wash the combined organic solution with 10% citric acid (3x), saturated sodium bicarbonate (2x) and brine (2x), dry over $MgSO_4$ and evaporate the solvent. Chromatograph on silica gel, eluting with ethyl acetate:hexane (1:4) containing 1% triethylamine to obtain 1-(S)-methoxycarbonyl-5-(t-butoxycarbonylamino)pentyn-3-yl-(S)-alanine, t-butyl ester.

C. Add the product of Part B (3.5 g) to a stirred solution of 4M HCL in dioxane (25 ml) at 0° and stir for 0.5 hours. Evaporate the solvent and triturate the residue with ether to obtain 1-(S)-methoxycarbonyl-5-amino-pentyn-3-yl-(S)-alanine, t-butyl ester, hydrochloride.

D. Add N-methylmorpholine (1.5 g) to a solution of the product of Part C (2.9 g) in tetrahydrofuran at 0°. Add 6-chloro-3,4-dihydro-2-(phenylethyl)-2H-1,2,4-benzothiadiazine-7-sulfonyl chloride, S/-dioxide (3.9 g) (See Preparation 2) and stir the resulting mixture at room temperature overnight. Dilute the reaction mixture with ethyl acetate, wash with 0.5 N HCl (1x), saturated sodium bicarbonate (2x), and brine (1x), dry over $MgSO_4$ and evaporate the solvent. Chromatograph on silica gel, eluting with ethyl acetate:dichloromethane to obtain a residue.

E. Add the product of Part D (4.8 g) to a 4M solution of HCL in dioxane (100 ml) and stir the resulting mixture at room temperature overnight. Evaporate the solvent then triturate the residue with ether to obtain a residue.

F. Treat the product of Part E in a manner similar to that described in Example 3, Part F, first paragraph, substituting (S)-proline, t-butyl ester for the octahydro-1H-indole, to obtain a residue.

Purify the resultant residue by chromatography on silica gel, eluting with ethyl acetate:$CH_2Cl_2$. Combine the desired fractions and evaporate the solvent to obtain a residue.

G. Treat the product of Part F in a manner similar to that described in Example 3, Part G to obtain the title compound.

EXAMPLE 9

N-[S-[[6-CHLORO-3,4,-DIHYDRO-3-(2-PHENYLETHYL)-2H-1,2,4-BENZOTHIADIAZIN-7-YL]SULFONYLAMINO]-1-(S)-METHOXYCARBONYL)-(E)-PENTEN-3-YL]-(S)-ALANYL-(S)-PROLINE, S/-DIOXIDE,HYDROCHLORIDE

A. Add a solution of 1-N-acetylamino-1-(S)-carboxy-5-(t-butoxycarbonylamino)-3-pentyne (5 g) in tetrahydrofuran (20 ml) dropwise to a stirred solution of sodium (1.2 g) in liquid ammonia (1.2 L). After 2 h, add ammonium hydroxide and water. Remove the ammonia, dissolve the residue in ethyl acetate, wash with 0.5N HCl (2x) and brine (3x), dry over $MgSO_4$ and evaporate the solvent. Purify by precipitation from dichloromethane as the DCHA salt of (E)-1-N-acetylamino-1-carboxy-5-(t-butoxy-carbonylamino)-3-pentene.

B. Add cobalt chloride hexahydrate (50 mg) and Acylase I (aminoacylase from porcine kidney, grade 1, available from Sigma Chemical Co., St. Louis, MO) (100 mg) to a stirred solution of the product of Part A (3.5 g) in 0.1M, pH 7.5 phosphate buffer (120 ml) at 38°. After 16 hours, remove the protein with activated carbon and filter through celite. Adjust pH of the solution to 2.75 and remove the unreacted isomer by washing with ethyl acetate (3x). Adjust the pH to 6.5 and evaporate the solvent. Remove the salt from the residue by dissolving in ethanol (100 ml) and filtering through celite. Evaporate the solvent to obtain (E)-1-amino-1-(S)-carboxy-5-(t-butoxycarbonylamino)-3-pentene.

C. Substitute the product of Part B (i.e., the 3-pentene compound) for the 3-pentyne compound in the procedure of Example 8, Parts B to G to obtain the title compound.

DESCRIPTION OF THE INVENTION

When topically administered to the eye, the compounds of the invention reduce intraocular pressure (IOP). For example, 1-[2-(S)-[[1-(S)-carboxy-5-[[6-chloro-3-chloromethyl-3,4-dihydro-2H-1,2,4-benzothiadiazinyl-7-yl]sulfonylamino]-pentyl]amino]-1oxopropyl]-[2S-(2α,3aα,7aα)]-octahydro-1H-indole-2carboxylic acid, S,S-dioxide caused falls in IOP of a magnitude similar to those produced by the anti-glaucoma agent timolol when each were administered at concentrations of 0.001 and 0.5 (w/v %), respectively, and tested by the following procedure:

Male New Zealand white rabbits having a normal IOP are conditioned to the laboratory setting for at least one 4 hr period before being used to study drug effects. A Makay-Marg applanation tonometer is used to measure IOP. Readings, in mm Hg, are taken in triplicate and the average is recorded.

Rabbits are restrained in a cloth sack 2 min. prior to IOP determination. The left lower eyelid is retracted to form a pouch and 1 drop of a local anesthetic is irrigated over the cornea. The lower eyelid is then held closed over the eye for about 1 min. Corneal anesthesia is repeated before each set of IOP determinations. Readings are taken just before dosing with drug (0 time) and at hourly intervals thereafter. Drugs are administered in a 50 ul volume in the same manner as the anesthetic.

The active compounds of the invention are administered in the form of ophthalmic pharmaceutical compositions adapted for topical administration to the eye; such as solutions, suspensions, ointments and solid inserts. Formulations of these compounds may contain from 0.00001 to 1.0%, preferably 0.00001 to 0.1%, and especially 0.00001 to 0.001% of medicament. Other concentrations may be employed provided the dose is effective in lowering intraocular pressure. As a unit dosage form, between 0.005 mcg to 0.5 mg, preferably 0.005 mcg to 50 mcg, and especially 0.005 mcg to 0.5 mcg of the active compound is applied to the human eye, generally on a daily basis. Individual dosage requirements are variable; however, and must be administered by the attending clinician on the basis of the severity of the disease and the condition and response of the patient.

To prepare suitable dosage forms, the active compounds may be conveniently admixed with a non-toxic pharmaceutically acceptable carrier suitable for topical ophthalmolgic administration. Typical of such pharmaceutically acceptable carriers are, for example, water, mixtures of water and watermiscible solvents such as lower alkanols or vegetable oils, petroleum based jelly, and including also from 0.1 to 2% by weight of hyroxyethyl cellulose, ethyl oleate, carboxymethyl cellulose, polyvinylpyrrolidone, and other water soluble ophthalmologically acceptable non-toxic polymers, for example, cellulose derivatives such as methyl cellulose, alkali metal carboxymethyl cellulose, hydroxyethyl cellulose, hydroxypropyl cellulose, hydroxypropylmethyl cellulose; acrylates such as polyacrylic acids salts, ethylacrylates; polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum and mixtures of these polymers. The pharmaceutical preparation may also contain non-toxic auxiliary substances such as emulsifying, preserving, wetting, bodying agents and the like, as for example, polyethylene glycols 200, 300, 400 and 600, carbowaxes 1,000, 1,500, 4,000, 6,000 and 10,000, antibacterial components such as quaternary ammonium compounds; phenylmercuric salts known to have cold sterilizing properties and which are non-injurious in use; thimerosal, methyl and propyl paraben, benzyl alcohol, phenyl ethanol; buffering ingredients such as alkali metal chloride, borate, acetate, gluconate buffers; antioxidants such as sodium metabisulfite, butylated hydroxyanisole (BHA), butylated hydroxytoluene (BHT) and the like; and other conventional ingredients such as sorbitan monolaurate, triethanolamine, oleate, polyoxyethylene sorbitan monopalmitylate, dioctyl alkali metal sulfosuccinate, monothioglycerol, ethylenediamine tetracetic acid and the like.

Additionally, suitable ophthalmic vehicles can be used as carrier media for the present purpose including conventional phosphate buffer vehicle systems, isotonic boric acid vehicles, isotonic alkali chloride vehicles, tris and the like.

The pharmaceutical preparation may also be in the form of a solid insert. For example, one may use a solid water soluble polymer as the carrier for the medicament. Inserts that are known in the art that are suitable for this use include those described in British Patent 15611, and in U.S. Pat. Nos. 3,993,071; 3,986,510; 3,868,445; and 3,867,510. Solid water insoluble inserts, such as those prepared from ethylene vinyl acetate copolymer, may also be utilized.

The compositions of the invention may include therapeutically effective amounts of additional ophthamologically acceptable therapeutic agents in addition to the compound of formula I. For example antibiotics and anesthetics, as well as other IOP lowering agents may be present.

The following is a non-limiting example of a topical ophthalmic formulation for use with compounds of the invention. The term "Drug" refers to 1-[2-(S)-[[1-(S)-carboxy-5-[[6-chloro-3-chloromethyl-3,4-dihydro-2H-1,2,4-benzothiadiazin-7-yl]sulfonylamino]pentyl-]amino]-1-oxopropyl]-[2S-(2α, 3aα, 7aα)]-octahydro-1H-indole-2-carboxlic acid, S,S-dioxide. It is contemplated, however, that therapeutically effective amounts of other compounds described in claim 1 may be substituted in its place.

EXAMPLE

| Topical Solution: | |
|---|---|
| Ingredients | mg/ml |
| Drug | 10.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sterile Water | q.s. ad 1.0 ml |
| 1. ON NaOH | q.s. ad pH 7.4 |

Mix the ingredients under sterile conditions and using standard techniques to obtain the opthamological solution.

We claim:

1. A topical ophthalmologically acceptable composition useful for reducing intraocular pressure which comprises an intraocular pressure reducing effective amount of a compound represented by the formula:

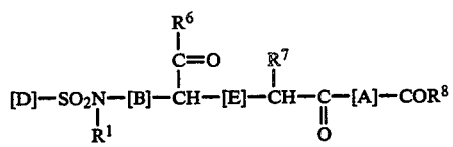

and the pharmaceutically acceptable salts thereof, wherein:

A is

[Structure IIa: -N-CH- with propyl chain]
[Structure IIb: -N-CH- with cyclohexyl group, (CH₂)$_p$ and (CH₂)$_q$]
[Structure IIc: -N-CH- with phenyl group, (CH₂)$_p$ and (CH₂)$_q$]

[Structure IId: dithiane with -N-CH-, (CH₂)$_n$ bridging two S, (CH₂)$_p$ and (CH₂)$_q$]
[Structure IIe: -N-CH- with branched alkyl (CH₂)$_k$]

K is 1 or 2;
n is 0 or 1;
p and q are 0, 1 or 2, provided that in structures IIb and IIc the sum of p and q is 1 or 2, and that in formula IId, p is not 0;
B is -[J]-[L]-[M]-;
D is

[Structure IIIa: benzene ring with -N(R²)-G- and -CH(R³)-NH- substituents, with R⁴ on ring]

E is —NH—, —O—, —S—, or —CH₂—;
G is —SO₂—;
J is —(CH₂)$_s$— or —((CH₂)$_t$—W)—;
L is a chemical bond, cis- or trans-lower alkene, lower alkyne, -Z-aryl-, -aryl-Z-, -Z-cycloalkyl-, or -cycloalkyl-Z-, wherein aryl is

[Three phenyl ring structures with R⁵ substituent]

and cycloalkyl is

[Cyclopentyl/cyclohexyl structures with R⁵ and (CH₂)$_w$]

wherein w is 1, 2 or 3;
M is —(CH₂)$_u$— or —((CH₂)$_t$—X—(CH₂)v)—;
W is $$-\overset{O}{\underset{\|}{C}}NH- \quad \text{or} \quad -NH\overset{O}{\underset{\|}{C}}-;$$

X and Z are independently a chemical bond, —NR⁹—, —O—, —S—, $$-\overset{O}{\underset{\|}{C}}NH- \quad \text{or} \quad -NH\overset{O}{\underset{\|}{C}}-;$$

s, u and v are independently 0–5;
t is 1–5;
R¹, R² and R⁹ are independently hydrogen, lower alkyl or lower acyl;
R³ is hydrogen, lower alkyl, halo- and dihaloloweralkyl, trifluoroethylthiomethyl, phenylloweralkyl, (cycloalkyl)loweralkyl, aminomethyl, loweralkylaminomethyl, phenyl(lower)alkylaminomethyl, (cycloalkyl)loweralkylaminomethyl, loweralkylthiomethyl or haloloweralkylthiomethyl;
R⁴ is chlorine or CF₃;
R⁵ is hydrogen, halogen, lower alkyl, lower acyl, lower alkoxy, haloloweralkyl or phenylloweralkyl;
R⁷ is hydrogen, lower alkyl or aminoloweralkyl;
R⁶ and R⁸ are independently hydroxy, alkoxy having from 1 to 8 carbon atoms, benzyl, allyl, R¹⁰—Q$_r$—(CH₂)$_m$—O—, wherein Q is oxygen or sulfur, r is 0 or 1 and m is 2 to 4, $$-\text{OCH}(R^{11})-\text{OCO}-\text{alkyl}$$

wherein the alkyl has from 3 to 8 carbon atoms, $$-\text{OCH}(R^{11})\text{CO}-\text{phenyl}$$

wherein the phenyl may be substituted with group T defined below, 1-glyceryl,

[Structure: benzoyl-O-CH(H)-O—] or —OCH₂—CH(O-)—CH₂(O-) with R¹² and R¹³

R¹⁰ is phenyl, substituted phenyl wherein the substituents are chosen from group T, 1-naphthyl or 2-naphthyl;
T is halogen, hydroxy, trifluoromethyl, lower alkoxy, lower alkyl, 2-furanyl, 3-furanyl, 2-thienyl, 3-thienyl, phenyl and substituted phenyl wherein the substituents are chosen from halogen, hydroxy, trifluoromethyl, lower alkoxy or lower alkyl;
R¹¹ is hydrogen or alkyl having from 1 to 8 carbon atoms;
R¹² is hydrogen, lower alkyl, unsubstituted or substituted phenyl and substituted or unsubstituted phenyl lower alkyl, wherein phenyl may be substituted by group T;
R¹³ is hydrogen or lower alkyl;
provided that if L is alkene or alkyne, J is —(CH₂)$_s$— wherein s is 1–5; provided that if L is -Z-aryl- or -Z-cycloalkyl-, J is —(CH₂)$_s$— wherein s is 2–5;

provided that if L is alkene, alkyne, -aryl-Z- or -cycloalkyl-Z-, M is —(CH₂)ᵤ— wherein u is 1-5; provided that if s and u are each zero, L is aryl or cycloalkyl (i.e. Z is a bond); and provided that if s and v are each zero, L is aryl or cycloalkyl (ie. Z is a bond);

in combination with an ophthamologically acceptable carrier for topical use.

2. A composition according to claim 1 wherein A is of the formula IIa, IIb wherein p is zero and q is 1, or IId wherein p and q are each 1 and n is zero.

3. A composition according to claim 1 wherein D is of the formula IIIa wherein G is —SO₂— and $R^4$ is chlorine.

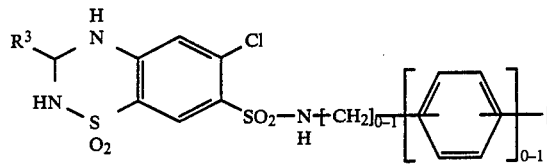

4. A composition according to claim 3 wherein $R^2$ is hydrogen and $R^3$ is phenylethyl, (cyclopentyl)methyl, butyl, pentyl, chloromethyl, dichloromethyl or trifluoroethylthiomethyl.

5. A composition according to claim 1 wherein E is —NH—.

6. A composition according to claim 1 wherein $R^7$ is hydrogen, methyl or aminobutyl.

7. A composition according to claim 1 wherein $R^6$ and $R^8$ are hydroxy.

8. A composition according to claim 1 wherein B is

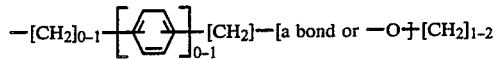

i.e., compounds wherein J is —(CH₂)ₛ— and s is 0-1, L is a bond or -Z-aryl- wherein Z is a bond, and M is —((CH₂)ₜ—X—(CH₂)ᵥ) wherein t is 1, v is 1-2 and X is a bond or —O—.

9. A composition according to claim 1 comprising a compound represented by the formula

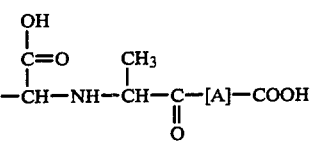

wherein A is formula IIa, IIb wherein p is 0 and q is 1, or IId wherein p and q are each 1 and n is 0, and $R^3$ is phenylethyl, chloromethyl, dichloromethyl, butyl, pentyl, (cyclopentyl)methyl, or trifluoroethylthiomethyl.

10. The composition of claim 1 wherein the compound is 1-[2-(S)-[[1(S)-carboxy-5-[[6-chloro-3-chloromethyl-3,4-dihydro-2H-1,2,4-benzothiadiazin-7-yl]sulfonylamino]pentyl]amino]-1-oxopropyl]-[2S(2α, 3aα,7aα)]-octahydro-1H-indole-2-carboxylic acid, S/-dioxide.

* * * * *